United States Patent
Stephens et al.

(10) Patent No.: US 10,450,530 B2
(45) Date of Patent: Oct. 22, 2019

(54) LUBRICATING MEMBERS FOR RAZOR CARTRIDGES

(71) Applicant: The Gillette Company, Boston, MA (US)

(72) Inventors: Alison Fiona Stephens, Maidenhead (GB); Coralie Claude Monique Rowe, Chertsey (GB)

( * ) Notice: Subject to any disclaimer, the term of this patent is extended or adjusted under 35 U.S.C. 154(b) by 0 days.

(21) Appl. No.: 15/193,172

(22) Filed: Jun. 27, 2016

(65) Prior Publication Data
US 2017/0002289 A1  Jan. 5, 2017

(30) Foreign Application Priority Data

Jun. 30, 2015 (EP) .................................... 15174442

(51) Int. Cl.
| | |
|---|---|
| *C10M 169/04* | (2006.01) |
| *A61K 8/31* | (2006.01) |
| *A61K 8/34* | (2006.01) |
| *A61Q 9/02* | (2006.01) |
| *A61K 8/86* | (2006.01) |
| *A61K 8/891* | (2006.01) |
| *A61K 8/894* | (2006.01) |
| *A61K 8/92* | (2006.01) |
| *A61K 8/02* | (2006.01) |
| *B26B 21/44* | (2006.01) |

(52) U.S. Cl.
CPC ........ *C10M 169/044* (2013.01); *A61K 8/0216* (2013.01); *A61K 8/31* (2013.01); *A61K 8/342* (2013.01); *A61K 8/86* (2013.01); *A61K 8/891* (2013.01); *A61K 8/894* (2013.01); *A61K 8/922* (2013.01); *A61Q 9/02* (2013.01); *B26B 21/443* (2013.01); *C10M 2203/102* (2013.01); *C10M 2207/021* (2013.01); *C10M 2209/104* (2013.01); *C10M 2229/025* (2013.01); *C10N 2250/08* (2013.01); *C10N 2270/00* (2013.01)

(58) Field of Classification Search
CPC ...... C10M 2229/025; C10M 2203/102; C10N 2250/08; C10N 2270/00
USPC ........................................................ 508/202
See application file for complete search history.

(56) References Cited

U.S. PATENT DOCUMENTS

| | | |
|---|---|---|
| 5,134,775 A | 8/1992 | Althaus et al. |
| 5,431,906 A | 7/1995 | Mohseni et al. |
| 5,711,076 A | 1/1998 | Yin et al. |
| 6,298,558 B1 | 10/2001 | Tseng et al. |
| 6,301,785 B1 | 10/2001 | Kwiecien et al. |
| 6,442,839 B1 | 9/2002 | Tseng et al. |
| 7,121,754 B2 | 10/2006 | Bressler et al. |
| 7,811,553 B2 | 10/2010 | O'Grady et al. |

(Continued)

OTHER PUBLICATIONS

EPO Search Report with Written Opinion in corresponding EPO application 15174442.2 dated Jan. 18, 2016.

*Primary Examiner* — Vishal V Vasisth
(74) *Attorney, Agent, or Firm* — Ronald Terk Sia; Kevin C. Johnson

(57) ABSTRACT

The invention relates to a lubricating member for a razor cartridge comprising a lipid phase comprising a lipophilic structurant and a liquid phase, wherein said liquid phase has a melting point below 45° C. and a water soluble polymer or mixture thereof which can be manufactured in a simple one batch process without thermal degradation and exhibiting improved lubricating and skin care properties over a sustained period.

8 Claims, 5 Drawing Sheets

(56) References Cited

U.S. PATENT DOCUMENTS

| | | |
|---|---|---|
| 8,524,207 B2 | 9/2013 | Ellis et al. |
| 2006/0225285 A1 | 10/2006 | Slavtcheff et al. |
| 2007/0110703 A1 | 5/2007 | O'Grady et al. |
| 2008/0060201 A1 | 3/2008 | Kwiecien |
| 2008/0081055 A1* | 4/2008 | Cassin ................. A61K 8/0208 424/401 |
| 2009/0117068 A1* | 5/2009 | Ellis ........................ A61K 8/02 424/70.12 |
| 2009/0223057 A1 | 9/2009 | Coope-Epstein et al. |
| 2013/0118014 A1* | 5/2013 | Stephens ............... B26B 21/443 30/41 |

* cited by examiner

LUBRICATING MEMBERS FOR RAZOR CARTRIDGES

FIELD OF THE INVENTION

The invention relates to lubricating members for razor cartridges comprising a water soluble polymer and a liquid phase which can be readily manufactured without impacting performance including lubricating properties.

BACKGROUND OF THE INVENTION

The use of shaving aids in combination with razor blades to provide lubrication benefits during the shave is known. See e.g., U.S. Pat. Nos. 7,121,754; 6,298,558; 5,711,076; 5,134,775; 6,301,785, U.S. 2009/0223057, US 2006/0225285, WO2007/031793 and U.S. Pat. No. 5,431,906. Such shaving aids typically comprise a water-insoluble matrix material to provide structural integrity and a water-soluble polymer, such as polyethylene oxide (polyox), in order to provide lubrication during the shave once the water-soluble polymer forms a solution with the water present during shaving. Since the introduction of polyox as a shaving lubricant, however little development has been made in the field, even though polyethylene oxide polymers are not without limitations. For example, the use of polyethylene oxide polymers having a low molecular weight only provides limited lubrication, and while improved lubrication may be seen when using polyethylene oxide polymer having higher molecular weights, this negatively impacts other aspects of the aqueous solution typically formed in-use. The resultant viscosity in aqueous solution may also increase, leading to negatively perceived attributes, for example concerning the feeling of the shave for the user, particularly in respect of the lubricant. The prior art does also describe the use of combinations of high and low molecular weight polyethylene oxide polymers in order to balance these performance attributes. Nevertheless, such combinations are also limited in their ability to improve performance and or suffer from other negative performance attributes. The art further describes the incorporation of additional materials to further improve the lubrication performance. For example U.S. Pat. No. 6,442,839 and US2007/0110703 describe the use of low levels of mineral and essential oils, butters, waxes and silicones. The use of mineral oil to enhance the glide performance is described in US2008/0060201. However the art also discloses that the presence of oils results in a reduction of the swelling and solubility of the shaving aid contained in water insoluble polymer matrix. The ability of the shaving aid to swell in contact with water is however believed to be the key mechanism by which the lubrication benefit is delivered to the skin. Hence this is not desirable, as it will negatively impact the overall performance. Thus oils are typically avoided in the matrix.

Another limitation of such shaving aids is related to the manufacturing process which typically involves an injection molding or extrusion process step. These processes require elevated temperatures in order to melt all the component materials and then subsequently mix them together and then injection mold or extrude. Consequently, the manufacture of such shaving aids is limited to low levels of additives and or materials which are not degraded by such process conditions. Nevertheless, the presence of even low levels of such additives in the manufacturing process can result in barrel slip and conveying inconsistencies which is also undesirable.

US2009/0223057 describes a razor shaving aid material that will last for an extended period of time and that can be manufactured at temperatures to avoid thermal degradation of ingredients, comprising a water soluble shaving aid, a water insoluble erodible medium that has a melting point above 45° C. and a molecular weight below 25000, wherein the water soluble shaving aid is soluble with the water insoluble erodible medium. The compatibility of the water soluble material and the water insoluble erodible material favorably influences the longevity of the shaving aid material. This manufacturing process is still complex however requiring multiple steps and component phase compatibility. Furthermore the improved longevity results in a shaving aid which is hard and brittle and which does not deposit sufficiently during use. Furthermore, the shaving aid is still also limited with regard to the addition of additives, which must also be compatible in the matrix.

Consequently there is still a need to provide a solid lubricating member for razor cartridges which can be manufactured in a simple one batch process comprising a water soluble polymer and a liquid phase contained therein exhibiting improved lubricating properties over a sustained period which can be readily manufactured without impacting performance due to thermal degradation of the ingredients and which can accommodate additional additives to provide desirable skin care benefits, especially in the liquid form such as oils.

SUMMARY OF THE INVENTION

One aspect of the invention relates to a lubricating member for use on a hair removal device, comprising from 20% to 90%, preferably from 20% to 80% by weight of a lipid phase, said lipid phase comprising:
a) from 10% to 70%, preferably from 10% to 60% by weight of a lipophilic structurant,
b) from 10% to 70% by weight of a liquid phase, contained within said lipophilic structurant
wherein said liquid phase has a melting point of 45° C. or less and
wherein said lubricating member further comprises from 1% to 40% by weight of a water soluble polymer or mixture thereof.

Another aspect of the invention relates to a method of manufacturing a lubricating member comprising the steps of
  i) Providing a particulate of said water soluble polymer,
  ii) Melting said lipophilic structurant,
  iii) Adding said liquid phase and mixing
  iv) Adding said water soluble polymer particles to said melted lipophilic structurant and liquid phase mixture and mixing
  v) Adding optional ingredients and mixing
  vi) Transferring the resultant mixture into a mould or container
  vii) Optionally cooling to 25° C.
Unless stated otherwise all % are given as weight % of the lubricating member.

DETAILED DESCRIPTION OF THE INVENTION

Lipid Phase

Figure 1:
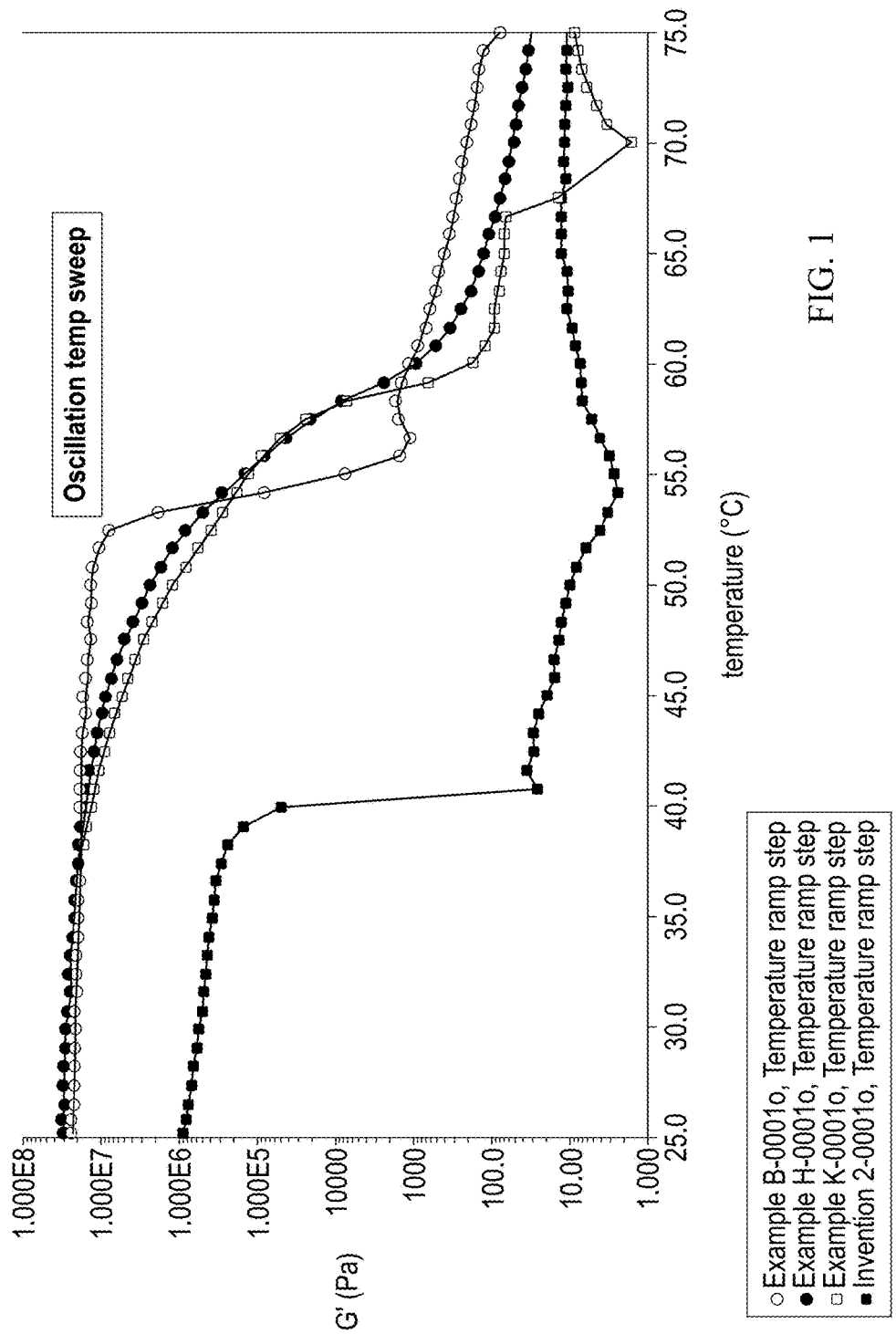
FIG. 1 and FIG. 2 show the rheology with respect to temperature of Inventive Example 2(B) and comparative examples B, H and K; graph 1 shows the oscillation temp sweep and Graph 2 shows the viscosity flow ramp as a function of temperature.

According to the invention the lubricating member is a solid lubricating member at 25° C. and comprises from about 20% to about 90% by weight, preferably from about 20% to about 80% by weight of a lipid phase. The lipid phase comprises a lipophilic structurant and a liquid phase contained within the lipophilic structurant. The lipid phase comprises from about 10% to about 70%, preferably from about 10% to 60%, more preferably from about 20% to about 40%, even more preferably from about 25% to about 35% by weight of the lubricating member of a lipophilic structurant.

The melting point of the lipophilic structurant is preferably greater than 45° C. to less than 60° C. and is thus preferably a solid at 25° C. The melting point is determined according to ASTM D5440-93. If the lipophilic structurant comprises more than one material, the melting point is determined for the resultant mixture as described hereinafter. In one embodiment the lipophilic structurant has a melting point of from about 45° C. to about 5° C. less than the melting point of said water soluble polymer. The lipophilic structurant is preferably water insoluble. It has been surprisingly found that by providing a lipophilic structurant having a melting point below 60° C. enables both the ready addition of liquid phase components and also water soluble polymers, which are immiscible therein without melting of the water soluble polymer during manufacture.

The later thereby avoids thermal degradation and thereby the lipophilic structurant provides a solid chassis at room temperature (25° C.) to contain the ingredient components which also deliver lubrication to the skin and other benefit agents during the shaving process. Moreover, the lipophilic structurant also enhances skin feel benefits.

Suitable lipophilic structurants for use herein include C14 or greater, preferably C14 to C20, more preferably C16 to C18 chain length fatty acyls such as fatty acids, fatty alcohols and esters, triglycerides, waxes and mixtures thereof. Particularly preferred are C14-C20 alcohols, in particular cetyl and stearyl alcohols and mixtures thereof.

Suitable lipophilic structurants also include natural, synthetic and silicone waxes. As used herein, the term "wax" includes, but is not limited to, any material that is solid at 45° C., preferably at 25° C.; and are very slightly soluble in water, preferably practically insoluble in water according to the United States' Pharmacopeia (USP) definition in 31/NF 26 Vol. 2 General Notices, Page Xvii. According to that definition, this means that 1000 to 10000 parts of water are needed to dissolve 1 part solute and that more than 10,000 parts of water are needed to dissolve 1 part solute respectively.

The lipophilic structurant and or lubricating member preferably comprises less than 5%, preferably less than 1% by weight and more preferably is substantially free of lathering soap (i.e. salts of fatty acids such as C4-30 carboxylic acids) or lathering surfactant. A lathering surfactant is defined as a surfactant which when combined with water and mechanically agitated generate a foam or later. Lathering surfactants include anionic and amphoteric lathering surfactants and mixtures thereof. Anionic lathering surfactants include sarcosinates, sulfates, sulfonate, isethionate, taurates, phosphates, lactylates, glutamates, alkali metal salts of fatty acids (i.e. soaps) having from 8 to 24 carbons, and mixtures thereof.

The wax may comprise natural wax, synthetic wax or mixtures thereof. Natural waxes may be plant, animal or mineral derived. Non-limiting examples of suitable natural waxes include Beeswax, Copernicia Cerifera (Carnauba) Wax, Euphorbia Cerifera (Candelilla) Wax, Jojoba Wax, Oryza Sativa (Rice) Bran Wax, Lemon peel wax, Soybean wax, Sunflower wax and mixtures thereof.

Non-limiting examples of suitable synthetic waxes include Hydrogenated Jojoba Wax, synthetic and siliconyl jojoba wax, Hydrogenated Microcrystalline Wax, Microcrystalline Wax, synthetic, siliconyl and Hydrogenated Rice Bran Wax, Ceresin, Ozokerite, Paraffin, benhenyl beeswax, synthetic, siliconyl and hydrogenated Beeswax, synthetic, hydrogenated and siliconyl Candelilla Wax, synthetic, hydrogenated and siliconyl Carnauba, wax, synthetic, hydrogenated and siliconyl lemon peel wax, synthetic, siliconyl and hydrogenated soybean wax, synthetic, siliconyl and hydrogenated sunflower wax and mixtures thereof. Preferred natural and synthetic waxes are Beeswax, Microcrystalline wax, Candellila wax, Ozokerite, and mixtures thereof.

Non-limiting examples of suitable silicone waxes include Stearyoxy trimethylsilane such as DC580 wax, C30-45 alkyl methicone available as DC AMS-C30 Cosmetic Wax, stearyoxymethyl silane available as DC Silkywax 10, C24-54 alkyl methicone such as DC ST-Wax 30, C30-45 Alkyldimethylsilyl, Polypropyl-silsesquioxane, available as DC SW-8005 resin wax, and mixtures thereof.

Particularly preferred lipophilic structurants may be selected from cetyl alcohol, stearyl alcohol, microcrystalline wax, stearyloxy trimethylsilane and mixtures thereof.

Liquid Phase

The lubricating member further comprises from about 10% to about 70%, preferably from about 10% to about 60%, more preferably from about 10% to about 40%, by weight of the lubricating member of a liquid phase. In one embodiment the liquid phase comprises a hydrophobic material or mixtures thereof. The liquid phase may provide a number of in use benefits such as lubrication, skin feel and cooling sensation. The liquid phase is contained within the solid lubricating member by the lipophilic structurant.

In one embodiment the liquid phase has a melting point of 45° C. or less, preferably 40° C. or less, even more preferably 30° C. or less, most preferably 25° C. or less. The melting point is determined according to ASTM D5440-93. Preferably the liquid phase and the hydrophobic material is liquid at 25° C. The use of a liquid phase enables the materials to be readily added to the lipophilic structurant upon melting thereof. In another preferred embodiment the liquid phase hydrophobic material or mixtures thereof may be very slightly soluble and have a melting point of 45° C. or less as defined herein above and be miscible with one another. In another embodiment the melting point of the mixture of liquid phase and the lipophilic structurant is preferably from 45° C. to 5° C. less than the melting point of the water soluble polymer.

Suitable liquid phase components for use herein include for example natural oils, synthetic oils, silicone oils, petrolatum, triglycerides, butters or mixtures thereof. As used herein, the term "oil" includes, but is not limited to any non-aqueous substance that is very slightly soluble, preferably practically insoluble in water according to the United States' Pharmacopeia (USP) definition in 31/NF 26 Vol. 2 General Notices, Page Xvii. According to that definition, means that 1000 to 10000 parts of water are needed to dissolve 1 part solute and that more than 10,000 parts of water are needed to dissolve 1 part solute respectively and is liquid at 25° C. Petrolatum may be considered as a lipophilic structurant or a liquid phase due to its complex mixture of component materials. For the purposes of this invention petrolatum is considered as a liquid phase component.

The oil may be selected from natural oil, synthetic oil, silicone oil and mixtures thereof. Non-limiting examples of suitable natural oils include Acetylated Castor Oil, Acetylated Hydrogenated Castor Oil, Actinidia Chinensis (Kiwi), Seed Oil, Adansonia Digitata Oil, Aleurites Moluccana Seed Oil, Anacardium Occidentale (Cashew) Seed Oil, Arachis Hypogaea (Peanut) Oil, Arctium Lappa Seed Oil, Argania Spinosa Kernel Oil, Argemone Mexicana Oil, Avena Sativa (Oat) Kernel Oil, Bertholletia Excelsa Seed Oil, Borago Officinalis Seed Oil, Brassica Campestris (Rapeseed) Seed Oil, Calophyllum Tacamahaca Seed Oil, Camellia Japonica Seed Oil, Camellia Kissi Seed Oil, Camellia Oleifera Seed Oil, Canola Oil, Capylic/Capric/Lauric Triglyceride, Caprylic/Capric/Linoleic Triglyceride, Caprylic/Capric/Mystic/Stearic Triglyceride, Caprylic/Capric/Stearic Triglyceride, Caprylic/Capric Triglyceride, Carthamus Tinctorius (Hybrid Safflower) Seed Oil, Carthamus Tinctorius (Safflower) Seed Oil, Carum Carvi (Caraway) Seed Oil, Carya Illinoensis (Pecan) Seed Oil, Castor Oil Benzoate, Chenopodium Quinoa Seed Oil, Cibotium Barometz Oil, Citrullus Vulgaris (Watermelon) Seed Oil, Cocos Nucifera (Coconut) Oil, Cod Liver Oil, Coffea Arabica (Coffee) Seed Oil, Coix Lacryma-Jobi (Job's Tears) Seed Oil, Corylus Americana (Hazel) Seed Oil, Corylus Avellana (Hazel) Seed Oil, Cucumis Sativus (Cucumber) Oil, Cucurbita Pepo (Pumpkin) Seed Oil, Daucus Carota Sativa (Carrot) Seed Oil, Elaeis Guineensis (Palm) Kernel Oil, Elaeis Guineensis (Palm) Oil, Gossypium (Cotton) Seed Oil, Helianthus Annuus (Hybrid Sunflower) Oil, Helianthus Annuus (Sunflower) Seed Oil, Hippophae Rhamnoides Oil, Human Placental Lipids, Hydrogenated Canola Oil, Hydrogenated Castor Oil, Hydrogenated Castor Oil Laurate, Hydrogenated Castor Oil Triisostearate, Hydrogenated Coconut Oil, Hydrogenated Cottonseed Oil, Hydrogenated C12-18 Triglycerides, Hydrogenated Fish Oil, Hydrogenated Lard, Hydrogenated Menhaden Oil, Hydrogenated Mink Oil, Hydrogenated Olive Oil, Hydrogenated Orange Roughy Oil, Hydrogenated Palm Kernel Oil, Hydrogenated Palm Oil, Hydrogenated Peanut Oil, Hydrogenated Rapeseed Oil, Hydrogenated Shark Liver Oil, Hydrogenated Soybean Oil, Hydrogenated Sunflower Seed Oil, Hydrogenated Tallow, Hydrogenated Vegetable Oil, lsatis Tinctoria Seed Oil, Juglans Regia (Walnut) Seed Oil, Lauric/Palmitic/Oleic Triglyceride, Umnanthes Alba (Meadowfoam) Seed Oil, Unum Usitatissimum (Linseed) Seed Oil, Lupinus Albus Seed Oil, Macadamia Integrifolia Seed Oil, Macadamia Ternifolia Seed Oil, Maleated Soybean Oil, Mangifera Indica (Mango) Seed Oil, Marmot Oil, Melaleuca Alternifolia (Tea Tree) Leaf Oil, Melia Azadirachta Seed Oil, Melissa Officina lis (Balm Mint) Seed Oil, Menhaden Oil, Mink Oil, Moringa pterygosperma Seed Oil, Mortierella Oil, Neatsfoot Oil, Nelumbium Speciosum Flower Oil, Nigella Sativa Seed Oil, Oenothera Biennis (Evening Primrose) Oil, Olea Europaea (Olive) Fruit Oil, Olea Europaea (Olive) Husk Oil, Orange Roughy Oil, Orbignya Cohune Seed Oil, Orbignya Oleifera Seed Oil, Oryza Sativa (Rice) Bran Oil, Oryza Sativa (Rice) Germ Oil, Ostrich Oil, Oxidized Corn Oil, Oxidized Hazel Seed Oil, Papaver Orientale (Poppy) Seed Oil, Passiflora Edulis Seed Oil, Persea Gratissima (Avocado) Oil, Pistacia Vera Seed Oil, Placental Lipids, Prunus Amygdalus Amara (Bitter Almond) Kernel Oil, Prunus Amygdalus Dulcis (Sweet Almond) Oil, Prunus Armeniaca (Apricot) Kernel Oil, Prunus Avium (Sweet Cherry) Seed Oil, Prunus Cerasus (Bitter Cherry) Seed Oil, Prunus Persica (Peach) Kernel Oil, Pyrus Malus (Apple) Oil, Ribes Nigrum (Black Currant) Seed Oil, Ricinus Communis (Castor) Seed Oil, Rosa Canina Fruit Oil, Rosa Moschata Seed Oil, Salmon Oil, Salvia Hispanica Seed Oil, Santalum Album (Sandalwood) Seed Oil, Sesamum Indicum (Sesame) Seed Oil, Shark Liver Oil, Solanum Lycopersicum (Tomato) Seed Oil, Soybean Lipid, Sphingolipids, Taraktogenos Kurzii Seed Oil, Telphairia Pedata Oil, Vegetable Oil, Vitis Vinifera (Grape) Seed Oil, Zea Mays (Corn) Germ Oil, Zea Mays (Corn) Oil mineral oil and mixtures thereof.

Suitable synthetic oils include hydrocarbons, esters, alkanes, alkenes and mixtures thereof. Non-limiting examples include isopropyl palmitate, isopropyl stearate, isohexadecane, isododecane, polyglyceryl triisostearate and mixtures thereof.

Non-limiting examples of suitable silicone oils include dimethicones (including partial esters of dimethicones and fatty acids derived from natural/synthetic oils), cyclomethicones, phenylated silicones, phenyl trimethicones, trimethyl pentaphenyl trisiloxane, silicone polyether block copolymers and mixtures thereof.

Suitable silicone polyether copolymers may comprise from about 1% to 50%, by weight of polyethylene oxide, from about 20% to about 90% by weight of polypropylene oxide and from about 1% to about 20% by weight of silicone. Preferably the silicone polyether copolymer comprises at least about 40%, more preferably at least about 50%, most preferably at least about 60% by weight of polypropylene oxide. In addition, the silicone polyether copolymer preferably comprises at least about 10%, more preferably from at least about 15%, most preferably from about 15% to 30% by weight of polyethylene oxide. Furthermore, the silicone polyether block copolymer comprises from 1% to 20%, preferably 10% to 20%, more preferably about 15% by weight of silicone.

Whilst silicone polyether block copolymers are known in the art to provide a number of benefits such as foaming, defoaming, wetting, deaeration and lubricity, it has been now been surprisingly found that the selection of silicone block copolymers having from 20% to 90% by weight of polypropylene oxide and from 1% to 50% of polyethylene oxide unexpectedly further provide improved lubrication whilst ensuring the required level of water dispersion and or solubility verses silicone polyether block copolymers having less or no polypropylene oxide and more polyethylene oxide. Moreover, the use of such silicone block copolymers provides improved adhesion to the skin verses alternative materials such as copolymers of polyethylene oxide and polypropylene oxide. Furthermore, the inclusion of 1% to 20% of silicone by weight of the silicone polyether block copolymer surprisingly provides desirable levels of lubrication despite being present at low levels in the polymer.

The copolymers are block copolymers and may preferably have a pendant graft structure. The silicone polyether block copolymer preferably has a ratio of polyethylene oxide units to polypropylene oxide units of from 3.0 to 0.1, preferably from 2.0 to 0.1, more preferably from 0.6 to 0.25. The silicone polyether block copolymer preferably has a ratio of polyethylene oxide units to polypropylene oxide units to silicone units of from 20:65:15.

The silicone polyether copolymer may have a molecular weight of from about 10000 to about 19000, more preferably from about 10000 to 15000. Suitable silicone polyether copolymers are available from Momentive under the SILWETSφ trademark products including L7210, L7602, L7220, L7230, L7500, preferably L7210 and L7602.

Non-limiting examples of commercially available silicone oils include Dow Corning 200 fluid, Dow Corning 244, Dow Corning 245, Dow Corning 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.), the Viscasil series (sold by General Electric Company), SF 1075 methylphenyl fluid (sold by General Electric Company) and 556 Cosmetic Grade Fluid (sold by Dow Corning Corp.), Silshine 151 (sold by Momentive), PH1555 and PH1560 (sold by Dow Corning) and Silwets such as Silwets 7210, 7230 and 7220 (available from by Momentive).

Suitable triglycerides, may have the following formula:

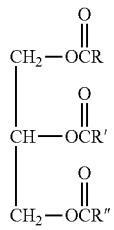

wherein R, R' and R" may be the same as or different from one or both of the others, wherein each of R, R' and R" is a fatty acid and wherein the or each triglyceride is solid at 25° C.

Suitable oils from which triglycerides may be formed from include, but are not limited to, the oils listed herein. Suitable fatty acids for formation of triglycerides include, but are not limited to, Myristoleic acid, Palmitoleic acid, Sapienic acid, Oleic acid, Linoleic acid, α-Linolenic acid, Arachidonic acid , Eicosapentaenoic acid, Docosahexaenoic acid, Lauric acid ($C_{12}$), Myristic acid ($C_{14}$), Palmitic acid ($C_{16}$), Stearic acid ($C_{18}$), Arachidic acid ($C_{20}$) and mixtures thereof.

Specific sources of triglycerides suitable for inclusion herein include Shea Butter, Theobroma Cacao (Cocoa) Seed Butter, Cocoa Butter, Mangifera Indica (Mango) Seed Butter, Kokum Butter and mixtures thereof. Particularly preferred are shea butter, cocoa butter and mixtures thereof.

Preferred liquid phase components may be selected from capric and or caprylic triglycerides, olive oil, shea butter, cocoa butter, petrolatum, isopropyl isostearate, dimethicones, phenylated silicones, silicone polyether block copolymers and mixtures thereof. The silicone polyether block polymers are particularly advantageous as they may facilitate the dispersion of the water soluble polymer in the lipophilic structurant as discussed hereinafter and may also improve lubrication.

Water Soluble Polymer

The lubricating member further comprises from about 1% to about 40% by weight, preferably from about 5% to about 40%, more preferably from about 10% to about 30% and even more preferably from about 20% to about 30% by weight of a water soluble polymer.

Examples of suitable water soluble polymers suitable for use hererin include polyethylene oxide, polyvinyl pyrrolidone, polyacrylamide, polyhydroxymethacrylate, polyvinyl imidazoline, polyethylene glycol, polyvinyl alcohol, polyhydroxyethymethacrylate, quaternary ammonium polymers, guars, celluloses, modified celluloses and mixtures thereof. In some embodiments the water soluble polymers may be selected from polyethylene oxide, polyvinyl pyrrolidone, polyacrylamide, polyhydroxymethacrylate, polyvinyl imidazoline, polyethylene glycol, polyvinyl alcohol, polyhydroxyethymethacrylate, quaternary ammonium polymers and mixtures thereof. In one embodiment, said water soluble polymer is selected from the group consisting of polyethylene oxide, polyethylene glycol, and mixtures thereof.

The preferred water soluble polymers are the polyethylene oxides generally known as POLYOX (available from Union Carbide Corporation) or ALKOX (available from Meisei Chemical Works, Kyoto, Japan). The water soluble polymer, (especially these polyethylene oxides), may have average molecular weights of at least about 20,000, preferably at least about 50,000, more preferably at least about 100,000 or from about 100,000 to about 8 million, preferably about 300,000 to about 5 million, more preferably from about 1 million to about 5 million, even more preferably from about 2 million to about 4 million. One preferred polyethylene oxide comprises a blend of about 40% to 80% of polyethylene oxide having an average molecular weight of about 5 million (e.g. POLYOX COAGULANT) and about 60% to 20% of polyethylene oxide having an average molecular weight of about 300,000 (e.g. POLYOX WSR-N-750). The polyethylene oxide blend may also advantageously contain up to about 10% (for example about 5%) by weight of a low molecular weight (i.e. MW<10,000) polyethylene glycol such as PEG-100.

Suitable water soluble cationic polymers are, for example, cationic cellulose derivatives, for example a quaternized hydroxymethyl cellulose obtainable under the name UCARE® Polymer JR 400 from Dow, hydrophobized quaternized hydroxymethyl cellulose, for example SOFTCAT® SL-5 from Dow, cationic starches, copolymers of diallylammonium salts and acrylamides, quaternized vinylpyrrolidone/vinyl imidazole polymers, for example LUVIQUAT® (BASF), condensation products of polyglycols and amines, quaternized collagen polypeptides, for example lauryldimonium hydroxypropyl hydrolyzed collagen (LAMEQUAT®L/Grünau), quaternised wheat polypeptides, polyethyleneimine, cationic silicone polymers, for example amidomethicones, copolymers of adipic acid and Dimethylaminohydroxyprophyldiethy-lenetriamine (CARTARETIN®/Clariant), copolymers of acrylic acid with dimethyldially-lammonium chloride (MERQUAT® 550/Chemviron), polyaminopolyamides, as described, for example, in FR-A-2 252840, and the cross-linked water-soluble polymers thereof, cationic chitin derivatives, for example of quaternised chitosan, optionally distributed as microcrystals; condensation products of dihaloalkyls, for example dibromobutane, with bisdialkylamines, for example bisdimethylamino-1,3-propane, cationic guar gum, for example JAGUAR® C-17 from Celanese or N-HANCE® 3196 from Ashland , quaternised ammonium salt polymers, for example MIRAPOL® A-15, MIRAPOL® AD-1, MIRAPOL® AZ-1 from Miranol.

The water soluble polymer is preferably selected so that it is solid at standard ambient temperature and pressure. The water soluble polymer may thus have a melting point of 60°

C. or greater, preferably 65° C. or greater more preferably 70° C. or greater. For embodiments comprising more than one water soluble polymer the melting point of each component preferably has a melting point of 60° C. or greater, preferably 65° C. or greater more preferably 70° C. or greater. The melting point is determined according to ASTM D5440-93.

In one embodiment of the invention the melting point of the lipophilic structurant (or mixture, if present) is at least 5° C., preferably at least 10° C. less than the melting point of the water soluble polymer, or from 5° C. to 45° C. less than the melting point of the water soluble polymer.

In another embodiment the water soluble polymer is provided in the form of particles, preferably discrete particles dispersed within the lipophilic structurant. Preferably at least 90%, more preferably at least 95% of said water soluble polymer is in the form of discrete particulates dispersed within said lipophilic structurant. These particulates may have an average particle size of from 50 to 1250 microns, preferably less than 1000 microns. The particles can be readily observed using scanning electron microscopy techniques Whilst not being bound by theory it is believed that lipophilic structurant having a melting point between about 45° C. or greater than 45° C. and less than 60° C., enables the water insoluble materials to be melted during the manufacturing process of the lubricating member in a simple hot melt one batch process, but at temperatures which allow the addition of thermally sensitive ingredients such as water soluble polymers without these materials being melted. Moreover it has been surprisingly found that the addition of the water soluble polymer does not require that the polymer is in a liquid form or that it is phase compatible with the lipophilic structurant. In fact is has been surprisingly found that by selecting a water soluble polymer having a melting point above the melting point of the lipophilic structurant, the water soluble material may be added in a solid form, as particulates which are dispersed throughout the lipophilic structurant. It is believed that consequently the water soluble material does not undergo any significant thermal degradation during manufacture thereby increasing its efficacy as a lubricant. Moreover using a particulate dispersion of the water soluble polymer obsoletes the need for high temperature and high shear process step during manufacture in order to incorporate within the lipophilic structurant. The dispersion of the water soluble polymer may be further improved by the incorporation of silicone polyether block polymers as one of the components of the liquid phase.

Water Insoluble Polymeric Structurant

The lubricating member comprises less than 5% by weight preferably less than 1% by weight, more preferably is substantially free of a water insoluble polymeric structurant. Whilst not bound by theory the structuring properties of the lubricating member of the present invention are provided by the lipophilic structurant and consequently additional water insoluble polymers are not required. Such water insoluble polymeric structurants include polyethylene (PE), polypropylene, polystyrene (PS), butadiene-styrene copolymer (e.g. medium and high impact polystyrene), polyacetal, acrylonitrile-butadiene-styrene copolymer, ethylene vinyl acetate copolymer, polyurethane, and blends thereof such as polypropylene/polystyrene blend or polystyrene/impact polystyrene blend.

Optional Ingredients

In some embodiments, the lubricating material may comprise any other ingredients commonly found in commercially available shaving aid members. The lubricating member may therefore contain other conventional shaving aid ingredients, such as low molecular weight water-soluble release enhancing agents such as polyethylene glycol (MW<10,000, e.g., 1-10% by weight PEG-100), water-swellable release enhancing agents such as cross-linked polyacrylics (e.g., 2-7% by weight), colorants, skin feel/care actives, surfactants, soaps (including interrupted soaps), antioxidants, preservatives, emollients, beard softeners, astringents, medicinal agents, plasticizers, additional lubricants, depilatories/keratolytic materials, tackifiers, skin-soothing agents, fragrances, compatibilisers, anti-inflammatory agents, antipruritic/counterirritant materials, dyes, pigments etc. and mixture thereof.

Other optional components may include skin active agents such as, but not limited to oil soluble vitamins, such as vitamin E derivatives, including vitamin E acetate and tocopherol nicotinate; oil-soluble vitamin A derivatives, such as retinyl palmitate; lanolin; ceramides; sterols and sterol esters; salicylic acid; camphor; eucalyptol; essential oils; peppermint oil, Iso E Super [(1-(1,2,3,4,5,6,7,8-octahydro-2,3,8,8-tetramethyl-2-naphthalenyl)ethanone]; and mixtures thereof. Particularly preferred are lanolin, essential oils, peppermint oil, coolants or senates and mixtures thereof. Suitable synthetic coolants include derivatives of or structurally related menthol compounds, i.e., containing the cyclohexane moiety, and derivatized with functional groups including carboxamide, ketal, ester, ether and alcohol. Non-limiting examples include methyl emthylamido oxalate, (under the tradename FRESCOLAT® X-cool available from Symrise), menthyl lactate (such as Frescolate ML Natural available from Symrise), and Menthyl Pyrrolidone Carboxylate also known as Menthyl PCA (under the tradename QUESTICES® available from Givaudan). Optional components which are liquids are included in determining the total amount of liquid phase present Method of Manufacture Another aspect of the invention relates to a method of manufacturing a lubricating member. The method comprises the steps of i) Providing a particulate of said water soluble polymer,
ii) Melting said lipophilic structurant, preferably at a temperature of less than about 90° C., more preferably between about 45° C. and about 60° C. whilst mixing,
iii) Adding said liquid phase and optional ingredients,
iv) Optionally cooling the mixture, preferably to about 60° C. or less and then adding said water soluble polymer particles to said melted lipophilic structurant and liquid phase mixture and mixing
vii) Adding other optional ingredients and mixing
viii) Transferring, for example pouring the resultant mixture into a mould or container
ix) Optionally cooling to about 25° C.

Hair Removal Head

According to some embodiments of the invention, the lubricating member finds particular application for hair removal devices. Hair removal devices generally comprise a hair removal head and a handle or grip portion, upon which the hair removal head is mounted. The hair removal device can be manual or power driven and can be used for wet and/or dry application. The hair removal head can include a wide scraping surface such as where the hair removal device is used with a depilatory, or be a razor cartridge or foil where the device is a shaving razor. The hair removal head may be replaceable and/or pivotally connected to a cartridge connecting structure and in turn or independently (e.g. permanently fixed) to a handle. In some embodiments, the cartridge connecting structure includes at least one arm to releasably engage the hair removal head.

The hair removal head typically comprises one or more elongated edges usually positioned between a first and second end, said one or more elongated edges comprising a tip extending towards said first end. Where the hair removal head is a razor cartridge the one or more elongated edges can include blades. For example, U.S. Pat. No. 7,168,173 generally describes a FUSION® razor that is commercially available from The Gillette Company and which includes a razor cartridge with multiple blades. Additionally, the razor cartridge may include a guard as well as a skin engaging member. A variety of razor cartridges can be used in accordance with the present invention. Non limiting examples of suitable razor cartridges, with and without fins, guards, and/or shave aids, include those marketed by The Gillette Company under the FUSION®, VENUS® product lines as well as those disclosed in U.S. Pat. Nos. 7,197,825, 6,449,849, 6,442,839, 6,301,785, 6,298,558; 6,161,288, and U.S. Patent Publ. 2008/060201. Those of skill in the art will understand that the lubricating member can be used with any currently marketed system or disposable razor, including those having 2, 3, 4 or 5 blades. In such a case, the hair removal device is a razor, the hair removal head is a razor cartridge and the one or more elongated edges are blades. Another example of a hair removal device is a scraping tool for use with a hair removal composition, i.e. a depilatory.

In some embodiments, said at least one lubricating member is located on the portion of the cartridge that contacts skin during the hair removal process, forward and/or aft of the blades. A feature "forward" of the one or more elongated edges, for example, is positioned so that the surface to be treated with by the hair removal device encounters the feature before it encounters the elongated edges. A feature "aft" of the elongated edge is positioned so that the surface to be treated by the hair removal device encounters the feature after it encounters the elongated edges. Where more than one lubricating member is provided on the hair removal device, they can be the same (identical) or different, in terms of physical shape/structure and/or chemical composition, and one or more of them may comprise the spray coated particulate.

In some particular embodiments, a plurality (e.g. 2, a first and second) of lubricating members may be provided on the hair removal head, with the first skin engaging member comprising the same composition or different. These lubricating members may be placed collectively (for example adjacent to one another) ahead of or behind the elongated edges (e.g. blades on a razor cartridge), including side by side, or separately with one ahead of the elongated edges and the other behind.

The lubricating member may be free standing utilizing a suitable attachment means such as adhesive or may be contained at least partially within a container.

The container typically has a base and at least one side wall extending vertically preferably perpendicular from said base and a skin contacting surface. In a preferred embodiment said container comprises a base and at least 2 side walls, more preferably at least 4 side walls, preferably said walls completely enclosing the base. Typically, each pair of walls are substantially parallel and preferably one pair of walls is substantially parallel to the at least two blades. Alternatively, the base may be enclosed by a one piece single wall. The container may form any shape including substantially rectangular, or oval. The container typically has a front wall adjacent the blades and a rear wall, preferably substantially parallel thereto and furthest from said blades.

The container is preferably further provided with at least one dispensing orifice for dispensing the lubricating member onto the skin during use. In one embodiment the container is provided with a top extending substantially perpendicular from the side wall (s). The container would in such an embodiment typically have a receiving region for receiving the lubricating member. The top may be substantially parallel to the base or it may be provide at an angle such that the distance of the top from the blade plane increases or decreases as the distance of the container from the blades increases. In one embodiment the height of the top of the container increases in distance from the blade plane as the container distance from the blades increases. In an alternative embodiment the height of the top of the container decreases in distance from the blade plane as the container distance from the blade increases.

The orifice may be of any shape and may, for example, have a cross sectional area of from about 0.00324 to about 1.613 $cm^2$. Small orifices can also be provided with cross sectional area of from about 0.0324 to about 0.324 $cm^2$, or from about 0.0645 to about 0.16135 $cm^2$. Larger orifices can have cross sectional areas of from about 0.324 to about 1.613 $cm^2$, or from about 0.645 to about 1.29 $cm^2$. The container may comprise a single orifice or multiple orifices which may be large and or small. In one embodiment the container comprises at least two orifices. Combinations of small and large orifices can also be provided on the same skin engaging member, or on separate members on the same cartridge, depending on the desired dispense rate and amount of exposure of the lubricating material to water. In one embodiment the top of the container is provide with one preferably two orifices, more preferably two substantially identical orifices adjacent one another.

In some embodiments, at least a portion of said container is not linear for example angled or curvilinear. Curvilinear as defined herein means that at least a portion is curved such that it does not form a straight line. Where at least two containers are provided, they can also be positioned relative to one another such that they do not form a straight line. Alternatively, the curved or angled nature is such that it forms at least a partial ring. A partial ring, as defined herein, means that the structure has at least two curved or angled sections which are concave to form an inner region. The partial ring can also include a curved or angled portion which is positioned convex to said inner region. One or more of said containers may also be positioned relative to one another to form a full ring.

The container can be formed of a variety of materials. The container may, preferably be for example, provided from a non-water soluble material such that it does not degrade or dissolve during normal use. The container typically has sufficient mechanical strength and rigidity to provide adequate mechanical strength to the entire skin engaging member, both as initially produced and after a significant amount of lubricating material has leached out of the container. Alternatively or in addition a further reinforcing member may also be utilized. In some embodiments, the container comprises a base and one or more side walls, forming a receiving region, or channel, onto or into which the lubricating material is placed.

The container may be made of a water-insoluble polymer, particularly a thermoplastic resin. Thermoplastic resins are those materials which can be extruded or molded into a shape and are resilient under normal environmental conditions such as contact with water, even up to normal household hot water temperatures (for example up to 125° C.); normal wear and tear by consumers during use; device assembly and shipping, etc. Thermoplastic resins suitable for use in the carrier include polystyrene, high impact polystyrene (polystyrene-butadiene), polypropylene, filled polypropylene, polyethylene, nylon ethylene vinyl acetate, and blends such as 70% nylon/30% polyethylene oxide, 60% polystyrene/40% polyethylene oxide butadiene styrene copolymer, polyacetal, acrylonitrile-butadiene styrene copolymer, and mixtures thereof. The preferred resins are high impact polystyrene, polystyrene, ethylene vinyl acetate (EVA), and mixtures thereof.

In some embodiments, the cartridge comprises a guard comprising at least one elongated flexible protrusion to engage a user's skin. The at least one flexible protrusion may comprise flexible fins generally parallel to said one or more elongated edges. Said at least one flexible protrusion may additionally or alternatively comprise flexible fins comprising at least one portion which is not generally parallel to said one or more elongated edges. Non-limiting examples of suitable guards include those used in current razor blades and include those disclosed in U.S. Pat. Nos. 7,607,230 and 7,024,776; (disclosing elastomeric / flexible fin bars); 2008/0034590 (disclosing curved guard fins); 2009/0049695A1 (disclosing an elastomeric guard having guard forming at least one passage extending between an upper surface and a lower surface). In some embodiments, said lubricating member is positioned on the cartridge aft of the guard and forward of said elongated edge. In another embodiment, the lubricating member is positioned on the cartridge forward of the guard. This embodiment can be particularly useful to deliver the lubricating member prior to contact with the guard.

INVENTIVE EXAMPLES

| Ingredient | Inventive 1 (wt. %) | Inventive 2 (wt. %) |
|---|---|---|
| Polyox 115M | 17.5 | 10 |
| Silwet L7210 | 52.5 | 60 |
| Multiwax 180MH | 5 | 5 |
| Cetyl alcohol | 25 | 25 |

Inventive Examples 1-2 were prepared as follows:
1. Sanitize all equipment
2. Turn on water bath/ vessel jacket to 85° C.
3. Add lipophilic structurants cetyl alcohol, multiwax 180MH) and stir with overhead stirrer until completely melted
4. Add oil phase ingredients (Silwet) and mix until fully liquid
5. Reduce heat to 55° C. and add powder ingredients (Polyox) until fully dispersed.

COMPARATIVE EXAMPLES

The following comparative examples are derived from US 2009/0223057 examples B, H and K and made according to the instructions therein.

| Ingredient | Example B (wt %) | Example H (wt %) | Example K (wt %) |
|---|---|---|---|
| Stearyl alcohol | 35 | 20 | 42.5 |
| Glyceryl hydroxystearate | 7.5 | — | 10 |
| Isostearic acid | 12.5 | — | — |
| Hydroxypropyl cellulose | 10 | — | 10 |
| Polyox coagulant | 27.5 | 15 | 17.5 |
| Polyox N-10 | 7.5 | — | — |
| Polyderm PPI-CO-200 | — | 57 | — |
| PVP/VA copolymer | — | — | 20 |
| Macadamia oil | — | 8 | — |

The rheology with respect to temperature of the inventive example 2 (B) and the comparative examples B, H and K was determined utilising a Rheometer ARG2 (TS). A disc was placed on the platform and a 1.26 mm gap is set. The samples were equilibrated at 25C and temperature ramp from 25° C. to 70° C. at a shear rate of (1/s) of 0.01 was conducted. The Viscosity (Pa·s) is recorded as a function of temperature.

An oscillation temperature sweep was also conducted over a temperature ramp of 25 to 70° C. (5° C./min) at 1 Hz frequency and an oscillation stress of 100 Pa.

Figure 2:
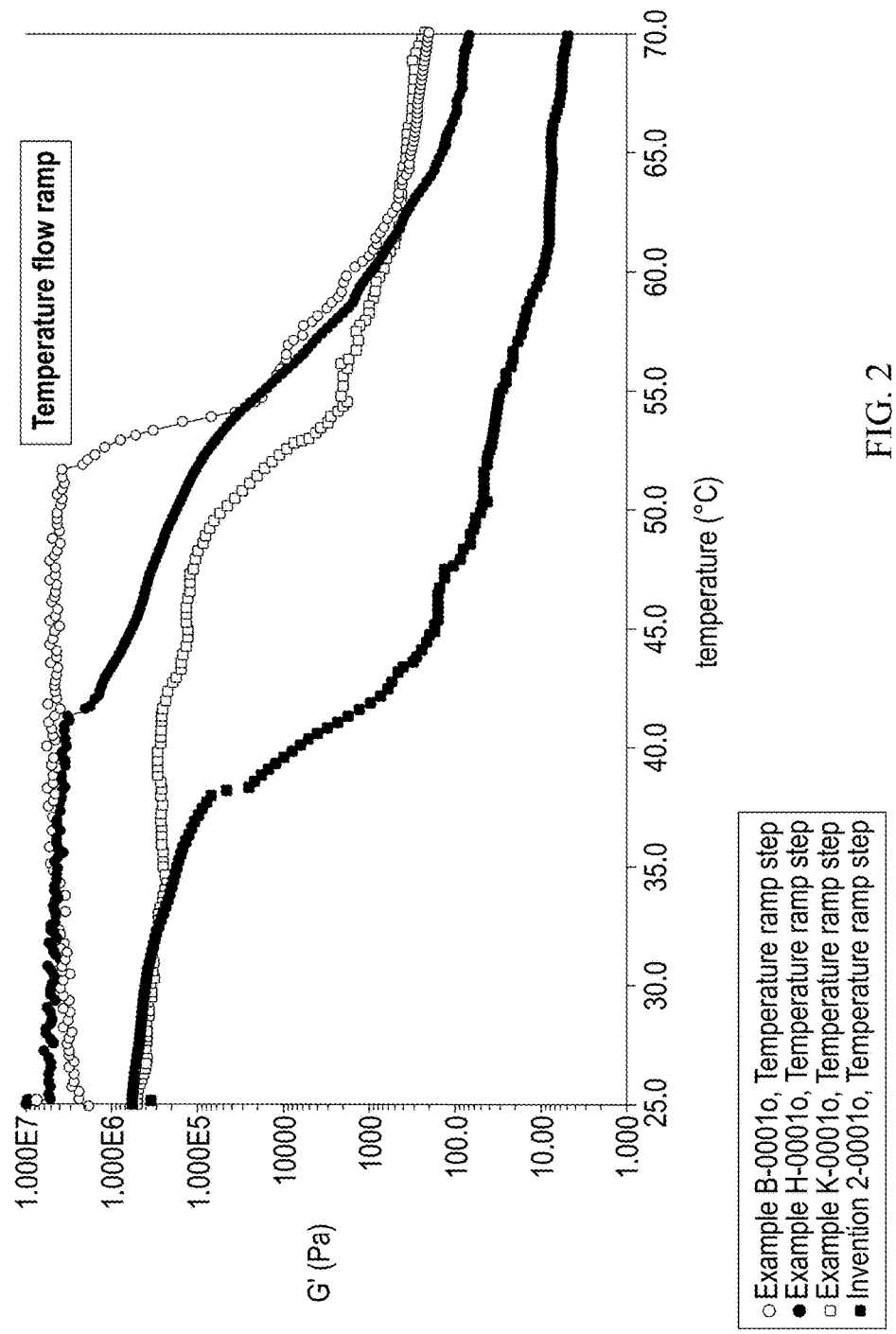

The results are given below and depicted graphically on FIGS. 1 and 2

Oscillation sweep data:

| Example K Temp ° C. | G' (Pa) | Example B Temp ° C. | G' (Pa) | Example H Temp ° C. | G' (Pa) | Invention 2 Temp ° C. | G' (Pa) |
|---|---|---|---|---|---|---|---|
| 25.3 | 3.08E+07 | 25.2 | 2.32E+07 | 25.3 | 2.92E+07 | 25.2 | 8.45E+05 |
| 25.9 | 3.04E+07 | 25.9 | 2.30E+07 | 25.9 | 3.17E+07 | 25.9 | 8.00E+05 |
| 26.5 | 2.69E+07 | 26.5 | 2.20E+07 | 26.5 | 2.87E+07 | 26.5 | 7.44E+05 |
| 27.4 | 2.93E+07 | 27.4 | 2.17E+07 | 27.4 | 2.97E+07 | 27.4 | 6.76E+05 |
| 28.3 | 2.69E+07 | 28.3 | 2.17E+07 | 28.3 | 3.03E+07 | 28.3 | 6.24E+05 |
| 29.1 | 2.85E-F07 | 29.1 | 2.10E+07 | 29.1 | 2.71E+07 | 29.1 | 5.79E+05 |
| 30 | 2.84E+07 | 29.9 | 2.10E+07 | 30 | 2.63E+07 | 30 | 5.35E+05 |
| 30.8 | 2.55E+07 | 30.8 | 2.19E+07 | 30.8 | 2.55E+07 | 30.8 | 5.02E+05 |
| 31.7 | 2.40E+07 | 31.7 | 2.11E+07 | 31.6 | 2.34E+07 | 31.6 | 4.72E+05 |
| 32.5 | 2.52E+07 | 32.5 | 2.03E+07 | 32.5 | 2.55E+07 | 32.5 | 4.46E+05 |
| 33.3 | 2.39E+07 | 33.3 | 2.04E+07 | 33.3 | 2.27E+07 | 33.3 | 4.20E+05 |
| 34.2 | 2.19E+07 | 34.1 | 1.97E+07 | 34.1 | 2.24E+07 | 34.1 | 3.97E+05 |
| 35 | 2.24E+07 | 35 | 1.93E+07 | 35 | 2.10E+07 | 35 | 3.71E+05 |
| 35.8 | 2.18E+07 | 35.8 | 1.94E+07 | 35.8 | 1.98E+07 | 35.8 | 3.48E+05 |
| 36.6 | 1.93E+07 | 36.7 | 1.92E+07 | 36.6 | 2.02E+07 | 36.7 | 3.23E+05 |
| 37.5 | 1.96E+07 | 37.5 | 1.86E+07 | 37.5 | 1.85E+07 | 37.5 | 2.89E+05 |
| 38.3 | 1.69E+07 | 38.3 | 1.89E+07 | 38.3 | 1.77E+07 | 38.3 | 2.29E+05 |
| 39.1 | 1.52E+07 | 39.2 | 1.77E+07 | 39.1 | 1.72E+07 | 39.1 | 1.49E+05 |

-continued

| Example K Temp °C. | G' (Pa) | Example B Temp °C. | G' (Pa) | Example H Temp °C. | G' (Pa) | Invention 2 Temp °C. | G' (Pa) |
| --- | --- | --- | --- | --- | --- | --- | --- |
| 40 | 1.32E+07 | 40 | 1.81E+07 | 40 | 1.54E+07 | 40 | 48620 |
| 40.8 | 1.27E+07 | 40.8 | 1.75E+07 | 40.8 | 1.43E+07 | 40.8 | 25.51 |
| 41.6 | 1.08E+07 | 41.6 | 1.75E+07 | 41.7 | 1.37E+07 | 41.7 | 34.38 |
| 42.5 | 9.02E+06 | 42.5 | 1.77E+07 | 42.5 | 1.19E+07 | 42.5 | 28.36 |
| 43.3 | 7.54E+06 | 43.3 | 1.68E+07 | 43.3 | 1.09E+07 | 43.3 | 28.44 |
| 44.2 | 6.33E+06 | 44.1 | 1.56E+07 | 44.2 | 9.40E+06 | 44.2 | 24.58 |
| 45 | 5.36E+06 | 45 | 1.58E+07 | 45 | 8.63E+06 | 45 | 19.27 |
| 45.8 | 4.35E+06 | 45.8 | 1.52E+07 | 45.8 | 6.99E+06 | 45.8 | 15.5 |
| 46.6 | 3.55E+06 | 46.7 | 1.50E+07 | 46.7 | 5.82E+06 | 46.6 | 15.52 |
| 47.5 | 2.76E+06 | 47.5 | 1.36E+07 | 47.5 | 4.57E+06 | 47.5 | 13.27 |
| 48.3 | 2.14E+06 | 48.3 | 1.45E+07 | 48.3 | 3.72E+06 | 48.3 | 12.73 |
| 49.2 | 1.60E+06 | 49.1 | 1.35E+07 | 49.2 | 2.85E+06 | 49.2 | 11.14 |
| 50 | 1.17E+06 | 50 | 1.35E+07 | 50 | 2.20E+06 | 50 | 9.618 |
| 50.9 | 7.96E+05 | 50.9 | 1.24E+07 | 50.9 | 1.63E+06 | 50.8 | 7.873 |
| 51.6 | 5.57E+05 | 51.6 | 1.02E+07 | 51.6 | 1.18E+06 | 51.7 | 6.085 |
| 52.5 | 3.89E+05 | 52.5 | 7.64E+06 | 52.5 | 7.73E+05 | 52.5 | 3.937 |
| 53.3 | 2.66E+05 | 53.3 | 1.78E+06 | 53.3 | 4.73E+05 | 53.3 | 3.121 |
| 54.2 | 1.83E+05 | 54.1 | 75170 | 54.2 | 2.64E+05 | 54.2 | 2.306 |
| 55 | 1.30E+05 | 55 | 6681 | 55.1 | 1.34E+05 | 55 | 2.476 |
| 55.9 | 84910 | 55.8 | 1487 | 55.8 | 76220 | 55.8 | 2.971 |
| 56.6 | 48050 | 56.7 | 1114 | 56.6 | 39270 | 56.6 | 4.02 |
| 57.5 | 22890 | 57.5 | 1417 | 57.5 | 19270 | 57.5 | 4.931 |
| 58.3 | 7007 | 58.3 | 1530 | 58.3 | 7884 | 58.3 | 6.513 |
| 59.2 | 619.8 | 59.2 | 1301 | 59.2 | 2258 | 59.2 | 7.025 |
| 60 | 169 | 60 | 1059 | 60 | 888 | 60 | 6.894 |
| 60.9 | 119.3 | 60.9 | 803.3 | 60.8 | 490.6 | 60.8 | 7.895 |
| 61.6 | 91.35 | 61.6 | 666.2 | 61.6 | 314.7 | 61.6 | 8.855 |
| 62.5 | 81.59 | 62.5 | 564.6 | 62.5 | 222.4 | 62.5 | 10.12 |
| 63.3 | 75.62 | 63.3 | 496.7 | 63.3 | 171.4 | 63.3 | 9.697 |
| 64.2 | 71.11 | 64.2 | 441 | 64.2 | 139.2 | 64.2 | 10.44 |
| 65 | 65.58 | 65 | 378.9 | 65 | 116.8 | 65 | 11.99 |
| 65.8 | 63.75 | 65.8 | 325.3 | 65.9 | 98.55 | 65.9 | 11.91 |
| 66.7 | 61.58 | 66.6 | 290.1 | 66.7 | 83.46 | 66.7 | 11.98 |
| 67.5 | 13.32 | 67.5 | 261.1 | 67.5 | 71.45 | 67.5 | 12.05 |
| 68.3 | −1.463 | 68.3 | 237.7 | 68.3 | 62.08 | 68.4 | 10.31 |
| 69.2 | −0.276 | 69.2 | 216.2 | 69.2 | 54.19 | 69.2 | 11.31 |
| 70 | 1.5 | 70 | 199.4 | 70 | 47.67 | 70 | 10.95 |
| 70.9 | 3.065 | 70.8 | 178.3 | 70.9 | 44.15 | 70.8 | 10.63 |
| 71.7 | 4.26 | 71.6 | 157.9 | 71.7 | 39.85 | 71.7 | 10.09 |
| 72.5 | 5.452 | 72.5 | 144.5 | 72.5 | 36.03 | 72.5 | 9.629 |
| 73.3 | 6.537 | 73.3 | 131.5 | 73.3 | 33.52 | 73.3 | 10.13 |
| 74.2 | 7.249 | 74.2 | 112.7 | 74.2 | 31.55 | 74.2 | 10.41 |
| 75 | 8.246 | 75 | 67.66 | 75.1 | 28.91 | 75.1 | 10.16 |

Flow temperature ramp data

| Example K viscosity Pa·s | Temp °C. | Example B viscosity Pa·s | Temp °C. | Example H viscosity Pa·s | Temp °C. | Invention 2 viscosity Pa·s | Temp °C. |
| --- | --- | --- | --- | --- | --- | --- | --- |
| 7.68E+05 | 25.1 | 2.28E+06 | 25.1 | 9.71E+06 | 25.2 | 8.52E+05 | 25.1 |
| 7.83E+05 | 25.4 | 2.90E+06 | 25.4 | 5.42E+06 | 25.4 | 8.14E+05 | 25.4 |
| 7.31E+05 | 25.7 | 2.85E+06 | 25.7 | 5.63E+06 | 25.7 | 7.99E+05 | 25.6 |
| 6.75E+05 | 25.9 | 3.38E+06 | 25.9 | 5.43E+06 | 25.9 | 7.86E+05 | 25.9 |
| 6.33E+05 | 26.2 | 3.11E+06 | 26.2 | 5.65E+06 | 26.2 | 7.82E+05 | 26.2 |
| 6.22E+05 | 26.4 | 3.11E+06 | 26.4 | 5.78E+06 | 26.4 | 7.72E+05 | 26.4 |
| 6.37E+05 | 26.7 | 3.42E+06 | 26.7 | 5.48E+06 | 26.7 | 7.72E+05 | 26.7 |
| 6.39E+05 | 27 | 3.35E+06 | 27 | 5.43E+06 | 27 | 7.54E+05 | 27 |
| 6.63E+05 | 27.2 | 3.43E+06 | 27.2 | 5.80E+06 | 27.2 | 7.44E+05 | 27.2 |
| 6.30E+05 | 27.5 | 3.64E+06 | 27.4 | 6.28E+06 | 27.5 | 7.35E+05 | 27.5 |
| 6.05E+05 | 27.7 | 3.80E+06 | 27.7 | 5.02E+06 | 27.7 | 7.33E+05 | 27.7 |
| 6.15E+05 | 28 | 3.63E+06 | 28 | 5.69E+06 | 27.9 | 7.16E+05 | 28 |
| 6.02E+05 | 28.2 | 3.36E+06 | 28.2 | 6.01E+06 | 28.2 | 7.08E+05 | 28.2 |
| 6.15E+05 | 28.5 | 4.01E+06 | 28.4 | 5.70E+06 | 28.5 | 6.95E+05 | 28.5 |
| 5.92E+05 | 28.7 | 3.54E+06 | 28.7 | 5.21E+06 | 28.7 | 6.82E+05 | 28.7 |
| 5.63E+05 | 29 | 3.43E+06 | 29 | 5.50E+06 | 29 | 6.70E+05 | 29 |
| 5.54E+05 | 29.3 | 4.06E+06 | 29.3 | 5.90E+06 | 29.3 | 6.57E+05 | 29.2 |
| 5.38E+05 | 29.5 | 3.79E+06 | 29.5 | 4.85E+06 | 29.5 | 6.42E+05 | 29.4 |
| 5.31E+05 | 29.7 | 3.98E+06 | 29.7 | 5.45E+06 | 29.7 | 6.33E+05 | 29.7 |
| 5.24E+05 | 29.9 | 4.14E+06 | 30 | 5.38E+06 | 30 | 6.23E+05 | 30 |
| 5.19E+05 | 30.2 | 4.29E+06 | 30.2 | 5.26E+06 | 30.2 | 6.06E+05 | 30.2 |

-continued

| Example K viscosity Pa·s | Temp °C. | Example B viscosity Pa·s | Temp °C. | Example H viscosity Pa·s | Temp °C. | Invention 2 viscosity Pa·s | Temp °C. |
|---|---|---|---|---|---|---|---|
| 5.09E+05 | 30.5 | 4.09E+06 | 30.5 | 4.67E+06 | 30.5 | 5.84E+05 | 30.5 |
| 5.05E+05 | 30.7 | 3.61E+06 | 30.7 | 5.32E+06 | 30.7 | 5.69E+05 | 30.8 |
| 5.14E+05 | 31 | 4.39E+06 | 31 | 5.58E+06 | 30.9 | 5.52E+05 | 31 |
| 5.11E+05 | 31.2 | 3.95E+06 | 31.2 | 4.56E+06 | 31.2 | 5.35E+05 | 31.2 |
| 5.00E+05 | 31.5 | 3.76E+06 | 31.5 | 4.96E+06 | 31.5 | 5.18E+05 | 31.5 |
| 4.96E+05 | 31.7 | 4.43E+06 | 31.7 | 5.28E+06 | 31.7 | 5.07E+05 | 31.7 |
| 4.93E+05 | 32 | 4.17E+06 | 32 | 5.43E+06 | 32 | 4.87E+05 | 32 |
| 4.85E+05 | 32.2 | 4.43E+06 | 32.2 | 4.61E+06 | 32.2 | 4.68E+05 | 32.2 |
| 4.68E+05 | 32.5 | 4.66E+06 | 32.5 | 5.21E+06 | 32.5 | 4.54E+05 | 32.5 |
| 4.53E+05 | 32.7 | 4.83E+06 | 32.7 | 5.45E+06 | 32.7 | 4.36E+05 | 32.7 |
| 4.43E+05 | 33 | 4.66E+06 | 33 | 4.84E+06 | 33 | 4.20E+05 | 32.9 |
| 4.47E+05 | 33.3 | 3.86E+06 | 33.2 | 4.96E+06 | 33.2 | 4.02E+05 | 33.2 |
| 4.41E+05 | 33.5 | 4.62E+06 | 33.5 | 5.02E+06 | 33.5 | 3.88E+05 | 33.5 |
| 4.21E+05 | 33.7 | 4.33E+06 | 33.8 | 5.17E+06 | 33.7 | 3.69E+05 | 33.7 |
| 4.11E+05 | 34 | 4.07E+06 | 34 | 4.29E+06 | 34 | 3.54E+05 | 34 |
| 4.01E+05 | 34.2 | 4.80E+06 | 34.2 | 5.04E+06 | 34.2 | 3.40E+05 | 34.2 |
| 3.96E+05 | 34.5 | 4.55E+06 | 34.5 | 5.02E+06 | 34.5 | 3.22E+05 | 34.5 |
| 3.88E+05 | 34.7 | 4.95E+06 | 34.7 | 4.53E+06 | 34.7 | 3.08E+05 | 34.7 |
| 3.95E+05 | 35 | 5.04E+06 | 35 | 4.45E+06 | 35 | 2.95E+05 | 35 |
| 4.10E+05 | 35.2 | 5.27E+06 | 35.2 | 4.83E+06 | 35.2 | 2.81E+05 | 35.2 |
| 4.17E+05 | 35.5 | 4.96E+06 | 35.5 | 5.03E+06 | 35.5 | 2.64E+05 | 35.5 |
| 4.21E+05 | 35.7 | 4.11E+06 | 35.7 | 4.17E+06 | 35.7 | 2.50E+05 | 35.7 |
| 4.23E+05 | 36 | 5.43E+06 | 35.9 | 4.69E+06 | 36 | 2.37E+05 | 36 |
| 4.27E+05 | 36.2 | 4.71E+06 | 36.2 | 4.86E+06 | 36.2 | 2.21E+05 | 36.2 |
| 4.34E+05 | 36.5 | 4.38E+06 | 36.5 | 4.71E+06 | 36.5 | 2.09E+05 | 36.5 |
| 4.35E+05 | 36.7 | 5.14E+06 | 36.7 | 4.34E+06 | 36.7 | 1.96E+05 | 36.7 |
| 4.41E+05 | 36.9 | 4.88E+06 | 37 | 4.62E+06 | 37 | 1.82E+05 | 37 |
| 4.40E+05 | 37.2 | 5.02E+06 | 37.2 | 4.76E+06 | 37.2 | 1.70E+05 | 37.2 |
| 4.43E+05 | 37.5 | 4.69E+06 | 37.4 | 4.17E+06 | 37.5 | 1.58E+05 | 37.5 |
| 4.37E+05 | 37.7 | 5.62E+06 | 37.7 | 4.46E+06 | 37.7 | 1.46E+05 | 37.7 |
| 4.40E+05 | 38 | 4.91E+06 | 38 | 4.39E+06 | 38 | 1.34E+05 | 38 |
| 4.40E+05 | 38.2 | 4.64E+06 | 38.2 | 4.39E+06 | 38.2 | 94540 | 38.3 |
| 4.38E+05 | 38.5 | 5.80E+06 | 38.5 | 3.89E+06 | 38.5 | 56320 | 38.5 |
| 4.54E+05 | 38.8 | 5.02E+06 | 38.8 | 4.39E+06 | 38.7 | 47960 | 38.7 |
| 4.60E+05 | 39 | 4.97E+06 | 39 | 4.35E+06 | 39 | 39640 | 39 |
| 4.62E+05 | 39.2 | 4.61E+06 | 39.2 | 3.94E+06 | 39.2 | 33990 | 39.2 |
| 4.68E+05 | 39.5 | 5.29E+06 | 39.5 | 3.93E+06 | 39.5 | 28840 | 39.5 |
| 4.70E+05 | 39.7 | 4.79E+06 | 39.7 | 4.13E+06 | 39.7 | 23710 | 39.7 |
| 4.77E+05 | 40 | 4.34E+06 | 40 | 4.19E+06 | 40 | 20100 | 40 |
| 4.68E+05 | 40.2 | 5.67E+06 | 40.2 | 3.70E+06 | 40.2 | 16330 | 40.2 |
| 4.66E+05 | 40.5 | 4.83E+06 | 40.5 | 3.95E+06 | 40.5 | 13400 | 40.5 |
| 4.54E+05 | 40.7 | 5.07E+06 | 40.7 | 4.06E+06 | 40.7 | 10740 | 40.7 |
| 4.39E+05 | 41 | 5.33E+06 | 41 | 3.90E+06 | 41 | 8587 | 41 |
| 4.34E+05 | 41.2 | 5.40E+06 | 41.2 | 3.61E+06 | 41.2 | 6778 | 41.2 |
| 4.26E+05 | 41.5 | 4.89E+06 | 41.5 | 3.63E+06 | 41.5 | 5533 | 41.5 |
| 4.21E+05 | 41.8 | 4.38E+06 | 41.8 | 2.35E+06 | 41.7 | 4018 | 41.8 |
| 4.06E+05 | 42 | 5.64E+06 | 42 | 2.06E+06 | 42 | 3235 | 42 |
| 3.80E+05 | 42.2 | 4.74E+06 | 42.2 | 1.89E+06 | 42.2 | 2706 | 42.2 |
| 3.56E+05 | 42.5 | 4.63E+06 | 42.5 | 1.71E+06 | 42.5 | 2660 | 42.5 |
| 3.30E+05 | 42.7 | 4.89E+06 | 42.7 | 1.61E+06 | 42.7 | 2317 | 42.7 |
| 3.11E+05 | 43 | 4.93E+06 | 43 | 1.49E+06 | 43 | 2150 | 43 |
| 2.87E+05 | 43.2 | 4.73E+06 | 43.2 | 1.38E+06 | 43.2 | 1664 | 43.3 |
| 2.76E+05 | 43.5 | 4.48E+06 | 43.5 | 1.27E+06 | 43.5 | 1540 | 43.5 |
| 2.64E+05 | 43.7 | 5.52E+06 | 43.7 | 1.20E+06 | 43.7 | 1261 | 43.7 |
| 2.50E+05 | 44 | 4.63E+06 | 44 | 1.11E+06 | 44 | 1198 | 44 |
| 2.42E+05 | 44.2 | 4.75E+06 | 44.2 | 1.06E+06 | 44.2 | 1090 | 44.2 |
| 2.34E+05 | 44.5 | 5.39E+06 | 44.5 | 9.84E+05 | 44.5 | 979.6 | 44.5 |
| 2.30E+05 | 44.7 | 5.16E+06 | 44.7 | 9.28E+05 | 44.7 | 901.2 | 44.7 |
| 2.26E+05 | 45 | 4.87E+06 | 45 | 8.66E+05 | 45 | 793.5 | 45 |
| 2.34E+05 | 45.2 | 4.49E+06 | 45.2 | 8.18E+05 | 45.2 | 810 | 45.2 |
| 2.40E+05 | 45.5 | 5.45E+06 | 45.5 | 7.73E+05 | 45.5 | 747.1 | 45.5 |
| 2.34E+05 | 45.7 | 4.68E+06 | 45.7 | 7.30E+05 | 45.7 | 729.5 | 45.7 |
| 2.31E+05 | 46 | 4.54E+06 | 45.9 | 6.90E+05 | 46 | 709 | 46 |
| 2.21E+05 | 46.2 | 5.12E+06 | 46.2 | 6.61E+05 | 46.3 | 732.8 | 46.2 |
| 2.22E+05 | 46.5 | 4.83E+06 | 46.5 | 6.26E+05 | 46.5 | 694.9 | 46.5 |
| 2.14E+05 | 46.7 | 4.75E+06 | 46.7 | 5.92E+05 | 46.7 | 700.9 | 46.7 |
| 2.16E+05 | 47 | 4.72E+06 | 47 | 5.59E+05 | 47 | 689.2 | 47 |
| 2.19E+05 | 47.3 | 5.44E+06 | 47.2 | 5.34E+05 | 47.2 | 609 | 47.2 |
| 2.14E+05 | 47.5 | 4.69E+06 | 47.5 | 5.07E+05 | 47.5 | 596.5 | 47.5 |
| 2.06E+05 | 47.7 | 4.63E+06 | 47.7 | 4.88E+05 | 47.7 | 489.2 | 47.7 |
| 1.94E+05 | 48 | 5.23E+06 | 48 | 4.61E+05 | 48 | 430 | 48 |
| 1.85E+05 | 48.2 | 4.89E+06 | 48.2 | 4.38E+05 | 48.2 | 397.2 | 48.3 |
| 1.72E+05 | 48.5 | 4.60E+06 | 48.5 | 4.10E+05 | 48.5 | 391.9 | 48.5 |
| 1.62E+05 | 48.7 | 4.27E+06 | 48.7 | 3.91E+05 | 48.7 | 347.6 | 48.7 |

-continued

| Example K viscosity Pa·s | Temp °C. | Example B viscosity Pa·s | Temp °C. | Example H viscosity Pa·s | Temp °C. | Invention 2 viscosity Pa·s | Temp °C. |
|---|---|---|---|---|---|---|---|
| 1.55E+05 | 49 | 5.08E+06 | 49 | 3.73E+05 | 49 | 323.5 | 49 |
| 1.40E+05 | 49.2 | 4.37E+06 | 49.2 | 3.54E+05 | 49.2 | 314.3 | 49.2 |
| 1.27E+05 | 49.5 | 4.33E+06 | 49.5 | 3.32E+05 | 49.5 | 290.9 | 49.5 |
| 1.12E+05 | 49.7 | 4.46E+06 | 49.7 | 3.15E+05 | 49.7 | 296.4 | 49.8 |
| 98850 | 50 | 4.49E+06 | 50 | 2.93E+05 | 50 | 268 | 50 |
| 83460 | 50.2 | 4.19E+06 | 50.3 | 2.75E+05 | 50.2 | 254.1 | 50.2 |
| 72990 | 50.5 | 3.96E+06 | 50.5 | 2.57E+05 | 50.5 | 239.4 | 50.5 |
| 64050 | 50.8 | 4.56E+06 | 50.8 | 2.39E+05 | 50.7 | 246.4 | 50.7 |
| 57910 | 51 | 3.99E+06 | 51 | 2.25E+05 | 51 | 242 | 51 |
| 49820 | 51.2 | 3.92E+06 | 51.2 | 2.09E+05 | 51.2 | 247.8 | 51.2 |
| 42430 | 51.5 | 3.95E+06 | 51.5 | 1.91E+05 | 51.5 | 240.8 | 51.5 |
| 35540 | 51.7 | 4.02E+06 | 51.7 | 1.75E+05 | 51.7 | 242.7 | 51.8 |
| 29280 | 52 | 2.48E+06 | 52 | 1.61E+05 | 52 | 229.7 | 52 |
| 25960 | 52.2 | 2.20E+06 | 52.2 | 1.50E+05 | 52.2 | 233.9 | 52.2 |
| 21570 | 52.5 | 1.85E+06 | 52.5 | 1.34E+05 | 52.5 | 218.8 | 52.5 |
| 17260 | 52.7 | 1.48E+06 | 52.7 | 1.21E+05 | 52.7 | 207.2 | 52.7 |
| 14430 | 52.9 | 1.05E+06 | 53 | 1.09E+05 | 53 | 202.8 | 53 |
| 11130 | 53.2 | 7.22E+05 | 53.2 | 96420 | 53.2 | 198.8 | 53.2 |
| 9327 | 53.5 | 4.85E+05 | 53.5 | 84370 | 53.5 | 193 | 53.5 |
| 8346 | 53.8 | 2.40E+05 | 53.7 | 75820 | 53.8 | 186 | 53.8 |
| 7903 | 54 | 1.26E+05 | 54 | 66310 | 54 | 185.2 | 54 |
| 7088 | 54.2 | 74320 | 54.2 | 59310 | 54.2 | 184.5 | 54.2 |
| 5960 | 54.5 | 50050 | 54.5 | 51000 | 54.5 | 178 | 54.4 |
| 5739 | 54.8 | 38370 | 54.7 | 45510 | 54.7 | 173 | 54.7 |
| 6708 | 55 | 35210 | 55 | 39840 | 55 | 159.2 | 55 |
| 6254 | 55.2 | 32580 | 55.2 | 35270 | 55.2 | 150.5 | 55.2 |
| 6145 | 55.5 | 29250 | 55.5 | 30310 | 55.5 | 144.8 | 55.5 |
| 6122 | 55.7 | 27580 | 55.7 | 26240 | 55.7 | 143.2 | 55.7 |
| 5979 | 56 | 24750 | 56 | 22630 | 56 | 135.5 | 56 |
| 6320 | 56.2 | 23070 | 56.2 | 19420 | 56.2 | 122.7 | 56.2 |
| 5499 | 56.4 | 22170 | 56.5 | 16350 | 56.5 | 119.4 | 56.5 |
| 4605 | 56.7 | 21390 | 56.7 | 14480 | 56.7 | 117.3 | 56.7 |
| 4350 | 57 | 21060 | 57 | 12430 | 57 | 111.7 | 57 |
| 4385 | 57.2 | 17600 | 57.2 | 10580 | 57.3 | 108.7 | 57.2 |
| 4513 | 57.5 | 15300 | 57.5 | 9150 | 57.5 | 99.86 | 57.5 |
| 4145 | 57.8 | 14530 | 57.8 | 7880 | 57.8 | 95.83 | 57.8 |
| 3940 | 58 | 12310 | 57.9 | 7136 | 58 | 91.25 | 58 |
| 3543 | 58.2 | 10100 | 58.2 | 6293 | 58.2 | 88.22 | 58.2 |
| 3388 | 58.5 | 8528 | 58.5 | 5531 | 58.5 | 82.84 | 58.5 |
| 3349 | 58.7 | 7339 | 58.7 | 5064 | 58.7 | 78.45 | 58.8 |
| 3150 | 59 | 6587 | 59 | 4471 | 59 | 76.73 | 59 |
| 3030 | 59.2 | 6051 | 59.2 | 4063 | 59.3 | 75.33 | 59.2 |
| 2836 | 59.4 | 5776 | 59.5 | 3821 | 59.5 | 69.18 | 59.5 |
| 2717 | 59.7 | 5688 | 59.7 | 3350 | 59.7 | 65.67 | 59.7 |
| 2533 | 60 | 5464 | 60 | 3052 | 60 | 64.38 | 60 |
| 2394 | 60.2 | 4329 | 60.2 | 2819 | 60.2 | 61.27 | 60.2 |
| 2308 | 60.5 | 3583 | 60.5 | 2610 | 60.5 | 60.81 | 60.5 |
| 2147 | 60.8 | 3257 | 60.7 | 2477 | 60.7 | 57.72 | 60.8 |
| 2077 | 61 | 2878 | 61 | 2234 | 61 | 56.05 | 61 |
| 1909 | 61.2 | 2719 | 61.2 | 2051 | 61.2 | 55.47 | 61.2 |
| 1791 | 61.4 | 2731 | 61.5 | 1855 | 61.5 | 54.35 | 61.4 |
| 1741 | 61.7 | 2493 | 61.7 | 1736 | 61.7 | 53.9 | 61.7 |
| 1749 | 62 | 2254 | 62 | 1615 | 62 | 53.18 | 62 |
| 1721 | 62.2 | 2138 | 62.2 | 1479 | 62.3 | 52.32 | 62.3 |
| 1860 | 62.5 | 1904 | 62.5 | 1310 | 62.5 | 51 | 62.5 |
| 1815 | 62.8 | 1729 | 62.7 | 1238 | 62.7 | 48.81 | 62.7 |
| 1676 | 63 | 1557 | 63 | 1196 | 63 | 50.05 | 63 |
| 1669 | 63.2 | 1434 | 63.2 | 1033 | 63.2 | 47.91 | 63.2 |
| 1641 | 63.5 | 1386 | 63.5 | 943.4 | 63.5 | 49.65 | 63.5 |
| 1601 | 63.7 | 1338 | 63.7 | 891.3 | 63.7 | 49.25 | 63.7 |
| 1520 | 64 | 1314 | 64 | 799.4 | 64 | 48.37 | 64 |
| 1530 | 64.2 | 1270 | 64.2 | 734.2 | 64.3 | 48.68 | 64.2 |
| 1504 | 64.5 | 1271 | 64.5 | 701.6 | 64.5 | 48.87 | 64.5 |
| 1424 | 64.7 | 1251 | 64.8 | 679.7 | 64.7 | 49.82 | 64.7 |
| 1396 | 65 | 1237 | 65 | 606.5 | 64.9 | 47.74 | 65 |

-continued

| Example K viscosity Pa·s | Temp °C. | Example B viscosity Pa·s | Temp °C. | Example H viscosity Pa·s | Temp °C. | Invention 2 viscosity Pa·s | Temp °C. |
|---|---|---|---|---|---|---|---|
| 1375 | 65.2 | 1217 | 65.2 | 590.2 | 65.2 | 48.04 | 65.3 |
| 1392 | 65.5 | 1182 | 65.5 | 579.1 | 65.5 | 48.11 | 65.5 |
| 1391 | 65.8 | 1167 | 65.8 | 540.2 | 65.8 | 47.04 | 65.7 |
| 1372 | 66 | 1148 | 66 | 508.1 | 66 | 46.23 | 66 |
| 1339 | 66.2 | 1133 | 66.2 | 475.1 | 66.2 | 44.48 | 66.2 |
| 1266 | 66.5 | 1109 | 66.5 | 452.3 | 66.5 | 44.17 | 66.5 |
| 1260 | 66.7 | 1075 | 66.8 | 429.4 | 66.7 | 41.5 | 66.7 |
| 1242 | 67 | 1073 | 67 | 414.1 | 67 | 39.91 | 67 |
| 1236 | 67.2 | 1071 | 67.2 | 412 | 67.2 | 41 | 67.2 |
| 1223 | 67.5 | 1042 | 67.5 | 396.4 | 67.5 | 38.98 | 67.5 |
| 1195 | 67.7 | 1021 | 67.7 | 375.5 | 67.7 | 39.7 | 67.7 |
| 1174 | 68 | 1004 | 68 | 376.8 | 68 | 38.53 | 68 |
| 1154 | 68.2 | 980.2 | 68.2 | 368.3 | 68.3 | 39.05 | 68.2 |
| 1114 | 68.5 | 952.6 | 68.5 | 351 | 68.5 | 37.76 | 68.5 |
| 1128 | 68.8 | 928.1 | 68.7 | 353.5 | 68.7 | 36.58 | 68.8 |

From the results it can be clearly seen that the inventive examples increases viscosity at temperatures below that for the comparative examples. Consequently the inventive example formulation 2 will commence its phase transition before the comparative examples at lower temperatures enabling the addition materials to be added without melting and undergoing any thermal degradation.

Figure 3:
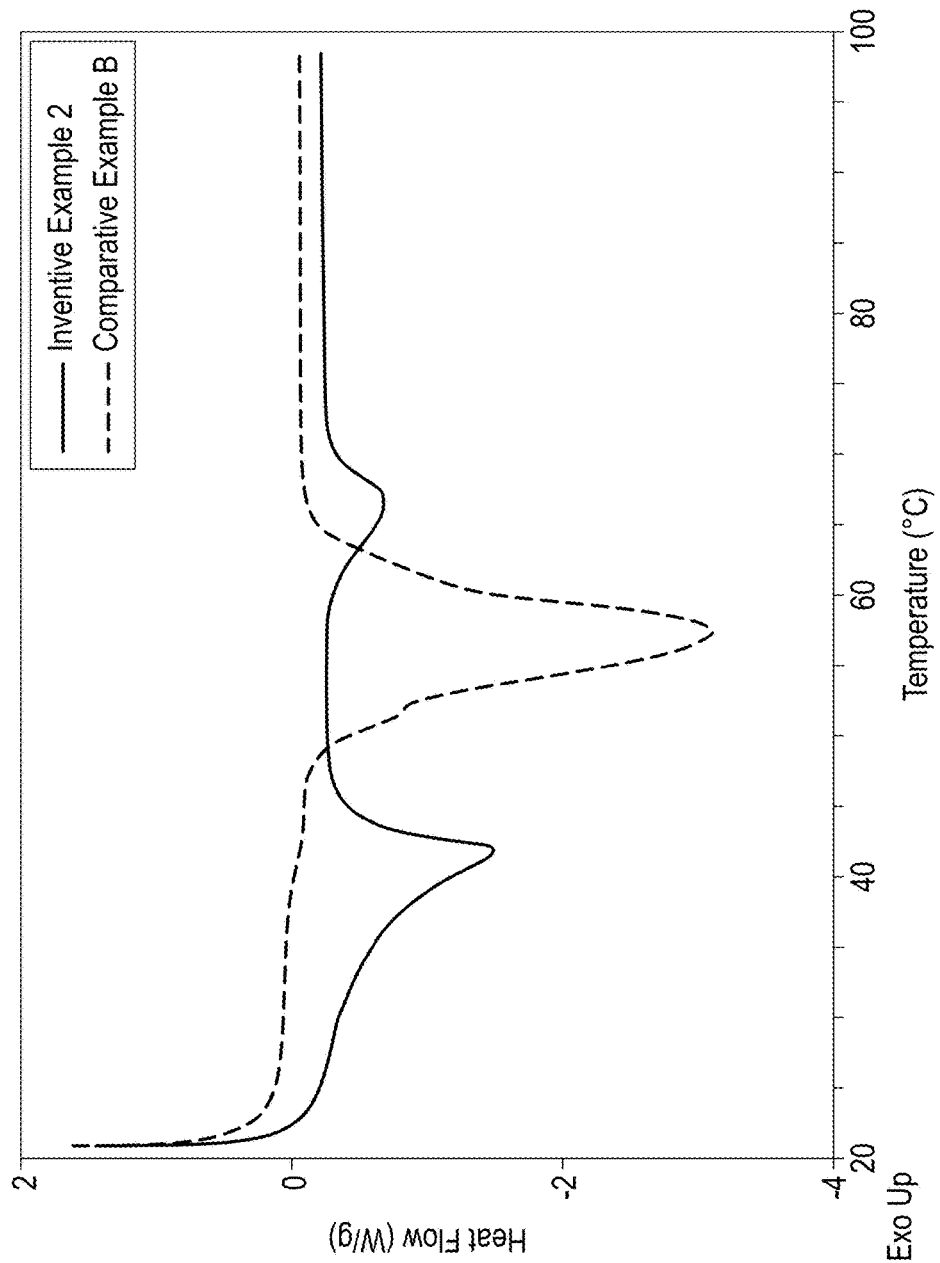
FIG. 3 is a graph of the transition temperature (heat flow verses temperature) of Inventive Example 2 and Comparative Example B.

The transition temperature for Comparative example B and Invention example 2 was determined using Differential Scanning calorimetry according to ASTM D3418 -15. Purge gas is Nitrogen at 50 ml/min As can be seen from FIG. 3 the Inventive example 2 Sample has two distinct melting events. The peaks coincide with the melting points of the lipophilic structurant and the water soluble polymer polyethylene oxide. This indicates that in the Inventive Sample the polyethylene oxide is present as a distinct phase and is not soluble in the lipophilic structurant. The comparative sample B has only one broad melting event indicating that one phase only is present and that the polyethylene oxide is in fact solubilised within the waxy erodible structurant phase.

In addition the effect of processing temperature on the water soluble polymer was analysed by microscopy. Two samples containing the same components as inventive example 2 (referred to as Inventive example 2*) in the following weight % was prepared as follows:

| Ingredient | Inventive example 2 * (Wt %) |
|---|---|
| Polyox 115M | 10 |
| Silwet L7210 | 70 |
| Multiwax 180MH | 3.33 |
| Cetyl alcohol | 16.7 |

Sterilize and clean all equipment with ethanol, calibrate balance.
1. Turn on water bath to 85° C.
2. In a beaker, weigh cetyl alcohol and multiwax and stir until completely melted using a water bath.
3. Add silwet and stir until fully liquid.
4. Decrease water bath temperature to 55° C.
5. When batch temperature reaches 55° C., add polyox while carrying on stirring.
6. When fully homogenous, remove half of the batch and place in a clean container. Set aside until cool. Store container with sample A label.
7. Increase water bath temperature to 85° C. and carry on stirring the remaining batch.
8. After 15 mins. at 85° C. remove batch, set aside until fully cooled. Place and store in a clean container and label as Sample B.

Figure 4:
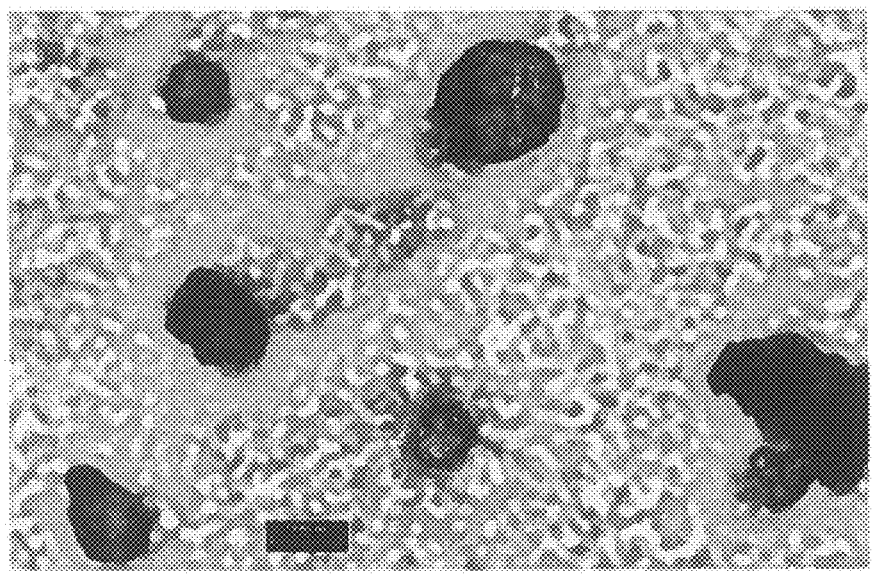
FIG. 4 and FIG. 5 are microscopic images of Inventive Example 2*A and B showing the presence and absence of particles.
Figure 5:
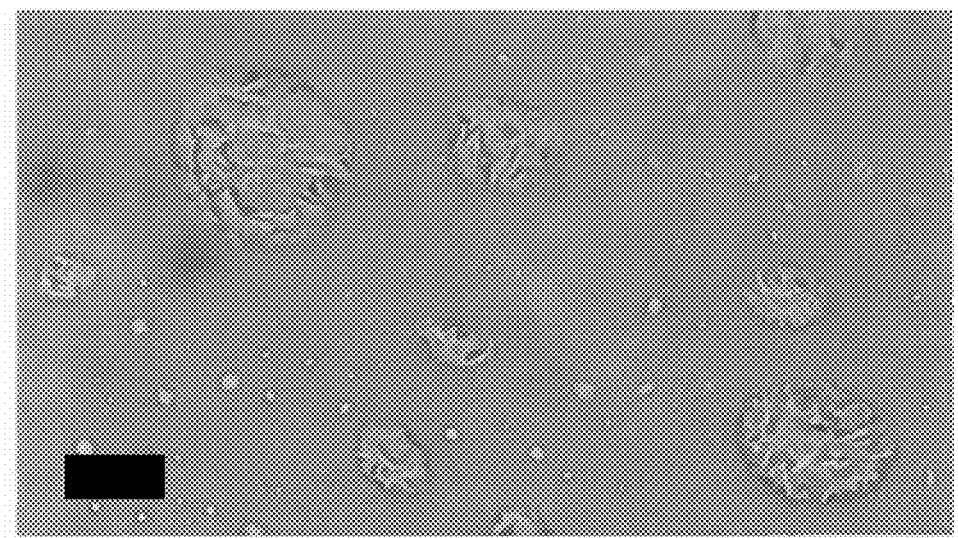

The samples A and B were prepared for microscopic analysis as follows:

Dissolve each sample in a few drops if n-hexane and shake until sample has dissolved. Place one drop of n-hexane solution of sample A or B under microscope such as Nikon Elipse E800 under polarised light with an objective lens of X10. Capture images using software image Pro MC. The resultant images are shown as FIGS. 4 and 5.

The images clearly show that the presence of particles in sample A verses sample B which has been heated to 85C.

Sensory Data

Sensory testing was conducted upon a naive panel (N=5) with 3-overlapping strokes being performed on their forearms for inventive example 1 and comparative example K. The order in which each panellist received the products and the first forearms used were randomized. The procedure used was as follows;

1. Wash both forearms thoroughly with warm water and soap to remove any oils or moisturizers that may already be on the skin.
2. Place product in water for 15 seconds (preheated to 40° C.)
3. Rinse one arm using water in the beaker provided (50 ml—preheated to 40° C.)
4. Take 3 overlapping strokes using the first plastic plaque of size (12 mm×40 mm) supplied.
5. Immediately assess lubrication of the product on a scale of 0-10; 0 being extremely draggy and 10 being extremely lubricating
6. Take three over strokes over the same area and reassess
7. Then assess stringiness on a scale of 0-10 rate: 0 being stringy and 10 being not stringy
8. Using your finger assess the skin condition on a scale of 0-10, 0 being sticky and 10 being not sticky.
9. Rinse fore-arm with 50ml of water in a beaker (pre heated to 40° C.) and pat dry three times with a paper towel and wait for 2mins. Then assess skin for sticky and not sticky on a 0-10 scale and not soft and soft on a 0-10 scale of 0 being not soft and 10 being soft.
10. Identify preferred product.

|  | Wet | | | | | | | Dry | | | | |
|---|---|---|---|---|---|---|---|---|---|---|---|---|
|  | Glide: | | | | | | | | | | | |
|  | Glide | | Over strokes | | Stringi-ness | | Sticki-ness | | Sticki-ness | | Softness | | Overall |
|  | 1 | K | 1 | K | 1 | K | 1 | K | 1 | K | 1 | K | preference |
| N1 | 4 | 7 | 6 | 7 | 10 | 0 | 9 | 6 | 10 | 10 | 8 | 8 | K |
| N2 | 8 | 8 | 9 | 9 | 3 | 6 | 7 | 4 | 10 | 10 | 7 | 7 | 1 |
| N3 | 8 | 9 | 8 | 9 | 6 | 5 | 6 | 6 | 10 | 10 | 8 | 9 | 1 |
| N4 | 7 | 8 | 7.5 | 9 | 7 | 9 | 9 | 9 | 10 | 10 | 7 | 7 | 1 |
| N5 | 8 | 8 | 8 | 8 | 4 | 3 | 7 | 7 | 10 | 10 | 7 | 7 | None |

From the above it can be seen that the inventive example 1 has an overall preference verses comparative example K.

Example formulations

| Ingredient | Example 1 (% w/w) | Example 2 (% w/w) | Example 3 (% w/w) |
|---|---|---|---|
| Polyox WSR coag | — | 10 | 20 |
| Polyox N60k | 30 | — | — |
| Silwet L7210 * | 20 | 50 | 20 |
| Softcat SL5 ** | — | — | 10 |
| Nhance 3196 *** | — | 10 | — |
| Petrolatum | — | — | 20 |
| DC200, 350 cst $ | 20 | — | — |
| Cetyl alcohol | 30 | 25 | 25 |
| Multiwax 180MH # | — | 5 | 5 |
| Total | 100 | 100 | 100 |

Suppliers:
* Momentive,
** Dow Chemicals,
*** Ashland,
$ Dow Corning,
Sonnenborn

| Ingredient | Example 4 (% w/w) | Example 5 (% w/w) | Example 6 (% w/w) | Example 7 (% w/w) | Example 8 (% w/w) |
|---|---|---|---|---|---|
| Polyox WSR coag | 35 | 10 | 20 | 5 | 5 |
| Polyox N60k | — | — | 15 | — | — |
| Silwet L7210 * | 45 | 70 | 10 | — | — |
| Softcat SL5 ** | — | — | — | — | — |
| Nhance 3196 *** | — | — | — | — | — |
| Petrolatum | — | — | — | — | — |
| DC200, 350 cst $ | — | — | — | 20 | 20 |
| Shea butter | — | — | 25 | — | — |
| Cetyl alcohol | 20 | 20 | 30 | 55 | 55 |
| Multiwax 180MH # | — | — | — | — | — |
| Total | 100 | 100 | 100 | 100 | 100 |

Formulation Examples 1-8 were prepared as follows:
1. Sanitize all equipment
2. Turn on water bath/ vessel jacket to 85° C.
3. Add lipophilic structurants (cetyl alcohol, multiwax 180MH) and stir with overhead stirrer until completely melted
4. Add oil phase ingredients (Silwet, petrolatum, DC200, shea butter) and mix until fully liquid
5. Reduce heat to 55° C. and add powder ingredients (Polyox, Nhance 3196, SoftCat) until fully dispersed.
6. Pour mixture into a mould
7. Assemble part onto razor cartridge.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition of the same term in a document incorporated by reference, the meaning of definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A lubricating member for a razor cartridge comprising from about 20% to about 90% by weight of a lipid phase, said lipid phase comprising:
 a) from about 10% to about 70% by weight of the lubricating member of a lipophilic structurant comprising:
  i) cetyl alcohol, stearyl alcohol, or mixture thereof, or
  ii) a microcrystalline wax; and
 b) from about 10% to about 70% by weight of the lubricating member of a liquid phase, wherein said liquid phase comprises a silicone polyether block copolymer comprising:
  i) a ratio of polyethylene oxide units to polypropylene oxide units to silicone units of 20:65:15, and
  ii) a molecular weight of from about 10000 to about 19000, and
wherein said lubricating member further comprises from about 20% to about 30% by weight of a water soluble polymer comprising polyethylene, and
wherein said lubricating member is substantially free of lathering soap or lathering surfactant, and wherein said lubricating member is formed by mixing said lipophilic structurant, said liquid phase, and said water soluble polymer.

2. A lubricating member according to claim 1, wherein at least about 90% of said water soluble polymer is in the form of discrete particulates dispersed within said lipophilic structurant.

3. A lubricating member for a razor cartridge according to claim 1, wherein said liquid phase further comprises a component selected from natural oil, synthetic oil, natural butters, triglycerides, petrolatum, silicones and mixtures thereof.

4. A lubricating member for a razor cartridge according to claim 1, comprising from about 25% to about 35% of said lipophilic structurant, from about 10% to about 40% of said liquid phase and from about 20% to about 30% of said water soluble polymer.

5. A lubricating member for a razor cartridge according to claim 1, wherein said member is substantially free of a water insoluble polymeric structurant.

6. A hair removal cartridge comprising a lubricating member according to claim 1.

7. A method of manufacturing a lubricating member according to claim 1, comprising the steps of
i) Providing a particulate of said water soluble polymer;
ii) Melting said lipophilic structurant;
iii) Adding said liquid phase and mixing;
iv) Adding said water soluble polymer particles to said melted lipophilic structurant and liquid phase mixture and mixing;
v) Adding any optional ingredients and mixing;
vi) Transferring the resultant mixture into a mould or a container; and
vii) Optionally cooling to about 25° C.

8. A razor cartridge with at least one blade, said razor cartridge comprising:
a) a lubricating member comprising from about 20% to about 90% by weight of a lipid phase, said lipid phase comprising:
i) from about 10% to about 70% by weight of the lubricating member of a lipophilic structurant comprising: (1) cetyl alcohol, stearyl alcohol, or mixture thereof, or (2) a microcrystalline wax; and
ii) from about 10% to about 70% by weight of the lubricating member of a liquid phase, wherein said liquid phase comprises a silicone polyether block copolymer comprising: (1) a ratio of polyethylene oxide units to polypropylene oxide units to silicone units of 20:65:15, and (2) a molecular weight of from about 10000 to about 19000, and
wherein said lubricating member further comprises from about 20% to about 30% by weight of a water soluble polymer comprising polyethylene, and
wherein said lubricating member is substantially free of lathering soap or lathering surfactant, and
b) a container comprising a base, a front wall adjacent to said at least one blade, and at least one side wall extending vertically from said base, wherein said lipid phase is at least partially contained within said container.

* * * * *